United States Patent
Mostofsky et al.

(10) Patent No.: US 10,410,041 B2
(45) Date of Patent: Sep. 10, 2019

(54) KINEMATIC AND MORPOMETRIC ANALYSIS OF DIGITIZED HANDWRITING TRACINGS

(71) Applicants: THE JOHNS HOPKINS UNIVERSITY, Baltimore, MD (US); KENNEDY KRIEGER INSTITUTE, INC., Baltimore, MD (US)

(72) Inventors: Stewart Mostofsky, Baltimore, MD (US); Benjamin Dirlikov, Kensington, MD (US); Michael I. Miller, Baltimore, MD (US); Elie Laurent Younes, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 271 days.

(21) Appl. No.: 15/310,637

(22) PCT Filed: May 12, 2015

(86) PCT No.: PCT/US2015/030270
§ 371 (c)(1),
(2) Date: Nov. 11, 2016

(87) PCT Pub. No.: WO2015/175462
PCT Pub. Date: Nov. 19, 2015

(65) Prior Publication Data
US 2017/0109566 A1   Apr. 20, 2017

Related U.S. Application Data

(60) Provisional application No. 61/991,675, filed on May 12, 2014.

(51) Int. Cl.
*G06K 9/00* (2006.01)
*A61B 5/16* (2006.01)
(Continued)

(52) U.S. Cl.
CPC ........ *G06K 9/00167* (2013.01); *A61B 5/1124* (2013.01); *A61B 5/16* (2013.01);
(Continued)

(58) Field of Classification Search
CPC .. A61B 5/00; A61B 5/16; A61B 5/103; A61B 5/11; A61B 5/408; A61B 5/1124;
(Continued)

(56) References Cited

U.S. PATENT DOCUMENTS

| | | | | |
|---|---|---|---|---|
| 5,562,104 A | * | 10/1996 | Hochberg | A61B 5/16 600/595 |
| 2005/0053269 A1 | * | 3/2005 | Franke | A61B 5/00 382/128 |
| 2011/0217679 A1 | * | 9/2011 | Rosenblum | A61B 5/11 434/155 |

FOREIGN PATENT DOCUMENTS

| | | |
|---|---|---|
| JP | 2007-079891 A | 3/2007 |
| KR | 10-1049152 B1 | 7/2011 |

OTHER PUBLICATIONS

Glaunès, Joan, et al. "Large deformation diffeomorphic metric curve mapping." International journal of computer vision 80.3 (2008): pp. 317-336.

* cited by examiner

Primary Examiner — Robert P Bullington
(74) Attorney, Agent, or Firm — Harrity & Harrity, LLP

(57) ABSTRACT

The present invention is directed to a computer application for analyzing handwriting. The handwriting is digitized by being captured by a computing device such as a tablet. The application analyzes four components of the digitized handwriting. The initial component provides real-time writing speed feedback to the subject. The second fully automated component computes a variety of kinematic measures based on periods of time when the subject is writing versus the pen
(Continued)

being off the tablet. A third component is able to concatenate pen strokes into user defined characters and assesses character and/or word spacing based on preset distances. For the fourth component, a 2-dimensional version of the large deformation diffeomorphic metric mapping (LDDMM) method is used to compare each character to a template character. Together, these components can be used to assess handwriting for a broad range of applications.

22 Claims, 9 Drawing Sheets

(51) Int. Cl.
*A61B 5/00* (2006.01)
*A61B 5/11* (2006.01)
*G09B 5/00* (2006.01)
*G09B 11/04* (2006.01)

(52) U.S. Cl.
CPC ............ *A61B 5/168* (2013.01); *A61B 5/6898* (2013.01); *A61B 5/7246* (2013.01); *A61B 5/7475* (2013.01); *G09B 5/00* (2013.01); *G09B 11/04* (2013.01)

(58) Field of Classification Search
CPC ..... A61B 5/168; A61B 5/6898; A61B 5/7246; A61B 5/7475; G06K 9/00167; G09B 5/00; G09B 11/04
USPC ....................................................... 434/155
See application file for complete search history.

ASD (Dark): r = -.62, p =.002
ADHD (Light): r = -.45 p = .042

ASD (green): r = -.70, p =.001

KINEMATIC AND MORPOMETRIC ANALYSIS OF DIGITIZED HANDWRITING TRACINGS

CROSS-REFERENCE TO RELATED APPLICATIONS

This application is a 35 U.S.C. § 371 U.S. national entry of International Application PCT/US2015/030270 having an international filing date of May 12, 2015 which claims the benefit of U.S. Provisional Application No. 61/991,675, filed May 12, 2014, the content of each of the aforementioned applications is herein incorporated by reference in their entirety.

GOVERNMENT SUPPORT

This invention was made with government support under 2 R01 NS048527-08, awarded by the National Institutes of Health. The government has certain rights in the invention.

FIELD OF THE INVENTION

The present invention relates generally to a medical computer application. More particularly, the present invention relates to a method for analyzing handwriting.

BACKGROUND OF THE INVENTION

Approximately 37% of children entering $2^{nd}$ grade present with handwriting impairments (i.e., dysgraphia). Children with a wide range of developmental disabilities, particularly autism spectrum disorders (ASD), Attention Deficit Hyperactivity Disorder (ADHD) and various learning disabilities, experience sustained difficulty with handwriting. In learning to write, children develop automaticity in handwriting, which minimizes the interference of motor demands with higher-order cognitive processes related to composition. Thus, the dynamics of writing account for a large portion of variance in composition fluency. Adults also present with handwriting difficulties and often handwriting is used to measure signs of motor impairments associated with neurodegenerative processes (e.g., resting tremor in Parkinson's disease). Due to the fundamental nature of handwriting, dysgraphia is one of the most common reasons for referral for occupational therapy.

For many years, handwriting assessment relied on manual methods with time consuming (often pain staking) analysis of letter form, size, and spacing that was subjective and only semi-quantitative. In recent years, computerized methods, involving recording from digitizing tablets, have been applied to more quantitative assessment of handwriting kinematics (e.g., speed, accelerations/decelerations); however, computerized assessment of letter form, which is one of, if not the most, crucial handwriting metric, have been lacking.

It would therefore be advantageous to provide a computer application to interventionists that could assess both kinematic and morphometric components of handwriting. This approach has been tested and shown to be sensitive to clinical differences in motor performance in ASD and ADHD. Therefore, this approach is not limited to readily implement and evaluate the efficacy of targeted interventions for handwriting. This approach could have a broader application. For example, it could be used in forensics to identify and individual's handwriting pattern, or to compare signatures to identify fraud or to provide easily accessible and implementable assessments of fine motor performance. This approach is able to assess any digital input and both analyze the kinematic and morphometric properties, thereby serving a broad set of applications.

SUMMARY OF THE INVENTION

The foregoing needs are met by the present invention, which provides a non-transitory computer readable medium programmed with steps including presenting a worksheet to a subject, wherein the worksheet comprises a number of template writing characters. The subject will be instructed to use a stylus. There will also be a prompt to enter information about the user such as age, identification, etc. The steps include prompting the subject to reproduce the template writing characters presented in the worksheet resulting in reproduced writing characters. Additionally, the steps include collecting data related to the reproduced writing characters and uploading the data related to the reproduced writing characters to a remote server. The remote server is programmed with steps including analyzing the data related to the reproduced characters, and transmitting an assessment of the reproduced characters.

In accordance with an aspect of the present invention, the non-transitory computer readable medium is further programmed with steps including an option to set a user defined speed threshold for prompting the subject to use an appropriate writing speed. The steps also include analyzing the data for morphometrics, such as overall form that reflects the degree of deformation required to match the reproduced writing character to the template writing character, overall size differences between the reproduced writing character and the template writing character, and overall pitch differences between the template writing character and the reproduced writing character. The steps include analyzing letter to letter spacing as well as letter to guideline spacing. The steps include analyzing the data for kinematics, such as speed of producing the reproduced writing characters, velocity inflections, acceleration and deceleration ratio, ballisticity, and spectral power. The data related to the reproduced writing characters can be uploaded to a cloud-type server. The steps further include analyzing both kinematics and morphometrics in parallel.

DETAILED DESCRIPTION

Figure 1:
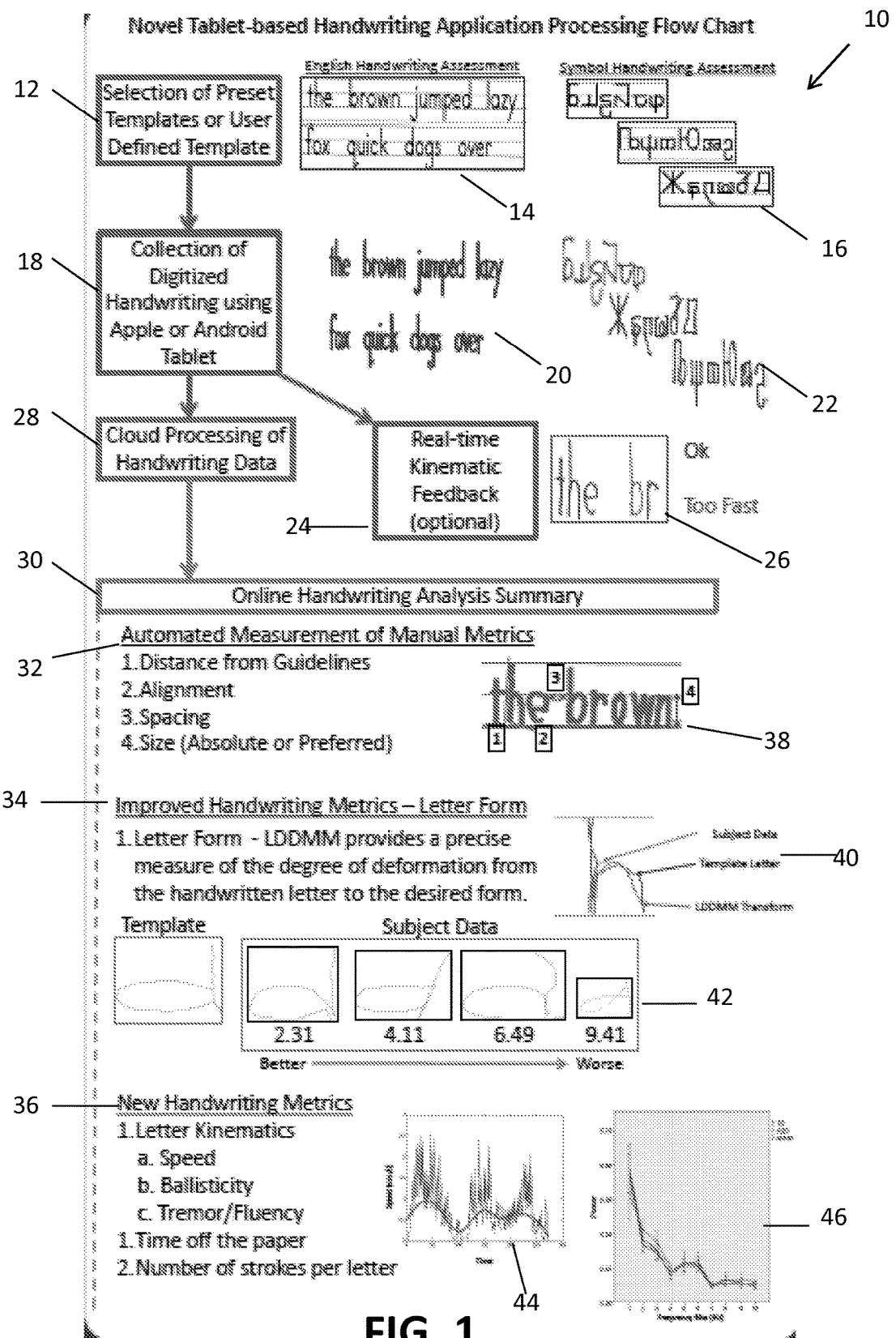
FIG. 1 illustrates a flow diagram showing an exemplary process for handwriting assessment, according to an embodiment of the present invention.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains, having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a computer application for analyzing handwriting. The handwriting is captured and digitized by a computing device such as a tablet. The application analyzes four components of the digitized handwriting. The primary component is a 2-dimension version of the large deformation diffeomorphic metric mapping (LDDMM) method and is used to compare each character to a template character. The 2-D LDDMM method assesses character (letter) form, size, and pitch. Additionally, two components assess handwriting kinematics, first during the collection of digitized handwriting and again during the cloud processing. The initial kinematic assessment computes real-time writing speed, on a letter by letter basis, in order to provide feedback to the subject; this utility will be optional. Once the digital handwriting assessment is completed, the cloud-based processing includes a fully automated component that computes a variety of kinematic measures (e.g. speed, ballisticity, spectral power, and motor fluency) based on periods of time when the subject is writing versus the pen being off the tablet. In order to assess morphometric and kinematic performance, a fourth component is able to concatenate pen strokes into user defined characters and assesses character and/or word spacing (e.g. letter to letter and letter to guideline spacing) based on preset distances. Together, these components can be used to assess handwriting in individuals with a wide range of other developmental disorders and acquired conditions associated with handwriting difficulties, or used to as part of a subject identification system.

The present invention limits local processing demands and allows users to collect handwriting data on a computing device that accepts user input in the form of handwriting, such as a tablet. An application according to an embodiment of the present invention includes a number of worksheets from which the user can choose, in order to perform one or more assessments. For example, there are approximately four preset handwriting worksheets, one composed of English alphabet characters, and a set of worksheets with non-English alphabet-like characters. Alternately, any number of worksheets could be provided, or users could upload their own worksheet using a drop down menu within the program on a non-transitory computer readable medium, therefore not limiting this application to English letter assessment. It is also possible that user generated worksheets could be made available after they are uploaded by a user, either immediately or after approval, in order to create a user generated database of worksheets. The user is prompted to select one of the worksheets or assessments in order to engage in a handwriting analysis. The user is also prompted to enter information, such as date, age, gender, ID number, name, etc. The worksheets can be selected by a medical professional, a therapist, parent or other person in order to assess a subject's handwriting, if the subject cannot do so himself. The professional, therapist, or patient can also be prompted to enter information about the subject, in case the subject is unable, too young, etc.

Once a worksheet is selected, the selected worksheet is presented on the tablet and the subject uses a stylus to copy or trace the characters. The stylus mimics writing with a traditional writing utensil, such as a pen or pencil. While a stylus is used as an example, any suitable device for mimicking writing could be used. Due to handwriting speed differences across children, the application includes an option to set a user defined speed threshold. This threshold will guide visual prompts informing the subject if they are writing too fast. Again, the speed can be entered by the user, a professional, or other adult. Then the assessment is given to the subject. The worksheets can take a variety of forms based on user language. The language can be set to any known language with various alphabets such as English, Spanish, or Chinese. The worksheet can also be symbol based to eliminate the need to select a specific language.

Once finished with the writing portion, the handwriting data, subject ID, user ID, and date is automatically uploaded to remote storage, such as a server or a cloud, for morphometric and kinematic processing. A program on a non-transitory computer readable medium is used to segment the data into information representing on-tablet versus off-tablet times and information representing coordinates (i.e. strokes). The strokes are automatically converted into letters using either predefined letter characteristics (e.g. letter curvature characteristics) or a machine learning algorithm that uses stroke subcomponent information to define each letter. The strokes data can be converted to letter data using a program on a non-transitory computer readable medium. Data is sent from the device receiving input to the program for analysis. The program can reside on the device receiving input or on a networked or remote device or cloud.

After each letter has been defined by the subject on the worksheet, the morphometric and kinematic analysis run in parallel. The morphometric analysis relies on 2-D Large Deformation Diffeomorphic Metric Mapping (LDDMM) to measure the morphological differences for each character by registering the subject's drawing of the character to a predefined template character. The dissimilarity between both the subjects character and the template character is measured by an overall letter form score as well as a size and pitch score. This analysis can be done by uploading the data for analysis by a program on a server or analyzing the data with a program residing directly on the device receiving input.

The novel morphometric analysis assesses: 1) Overall form that reflects the degree of deformation required to match the subject's character to the template, 2) Overall size differences, and 3) Overall pitch differences measured as the angular difference between subject and template characters. These metrics are analyzed by the program either on the computing device accepting the input or a remote computing device or server.

The kinematic analysis assesses: 1) Letter Speed (the time required for the subject to draw each letter), 2) Velocity Inflections—number of zero crossings in the velocity functions, 3) Acceleration/Deceleration Ratio—the proportion of time spent accelerating vs. decelerating, 4) Ballisticity—the number of zero crossings in the acceleration function divided by the number of zero crossings in the velocity function, 5) Spectral Power from 1-10 Hz which can be used to identify neuromotor noise (overall increases in power from 1-10 Hz) or increases in power at specific frequencies (used to assess tremors), and 6) Time off tablet—total amount of non-writing time. Additionally, the kinematic script assesses letter spacing (e.g., letter to letter and letter to guideline spacing) for the predefined MHA and set of non-English alphabet worksheets. An output file is then made available for the users to download at their convenience. The output file will include both absolute measurements, outlined above, as well as population normalized measures to track handwriting performance. The output file can be transmitted back to the user's profile on the computer application, to one or more email addresses, or accessed through a website associated with the application. These metrics are analyzed by the program either on the computing device accepting the input or a remote computing device or server.

Figure 2:
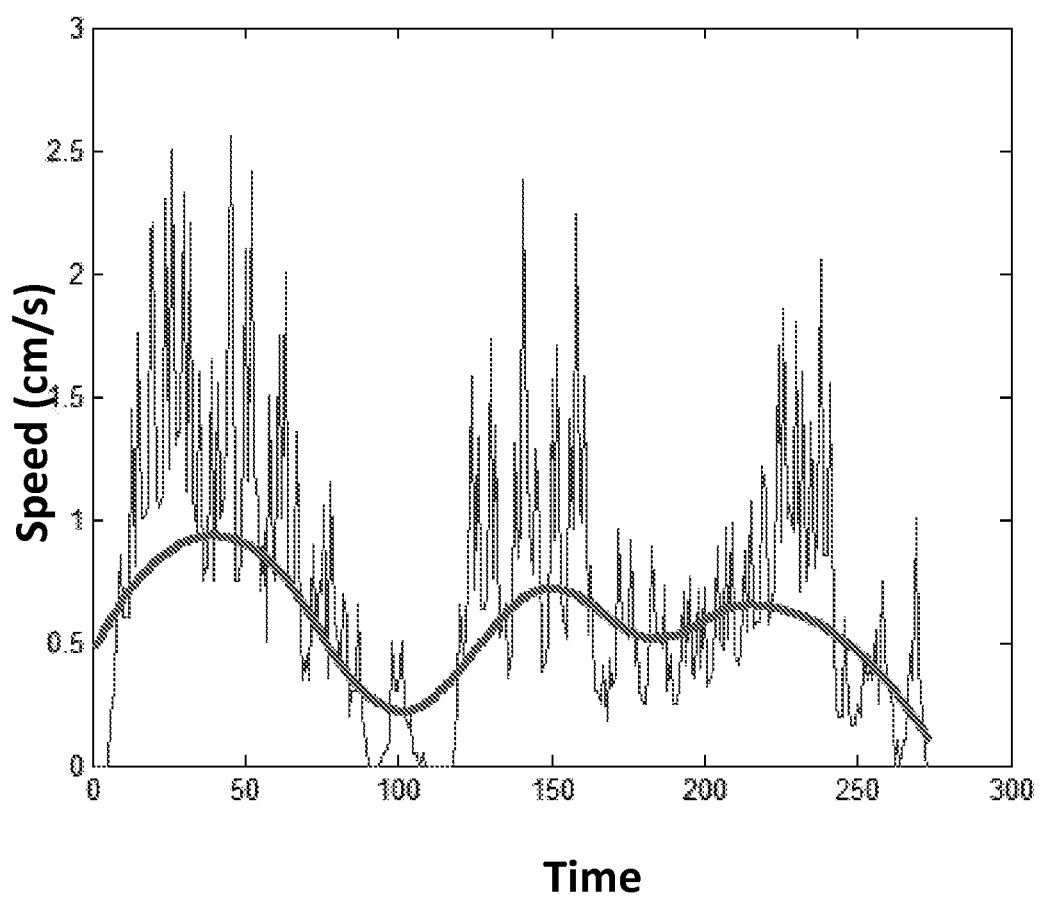
FIGS. 2 and 3 illustrate graphical views of new handwriting metrics, according to an embodiment of the present invention.
Figure 3:
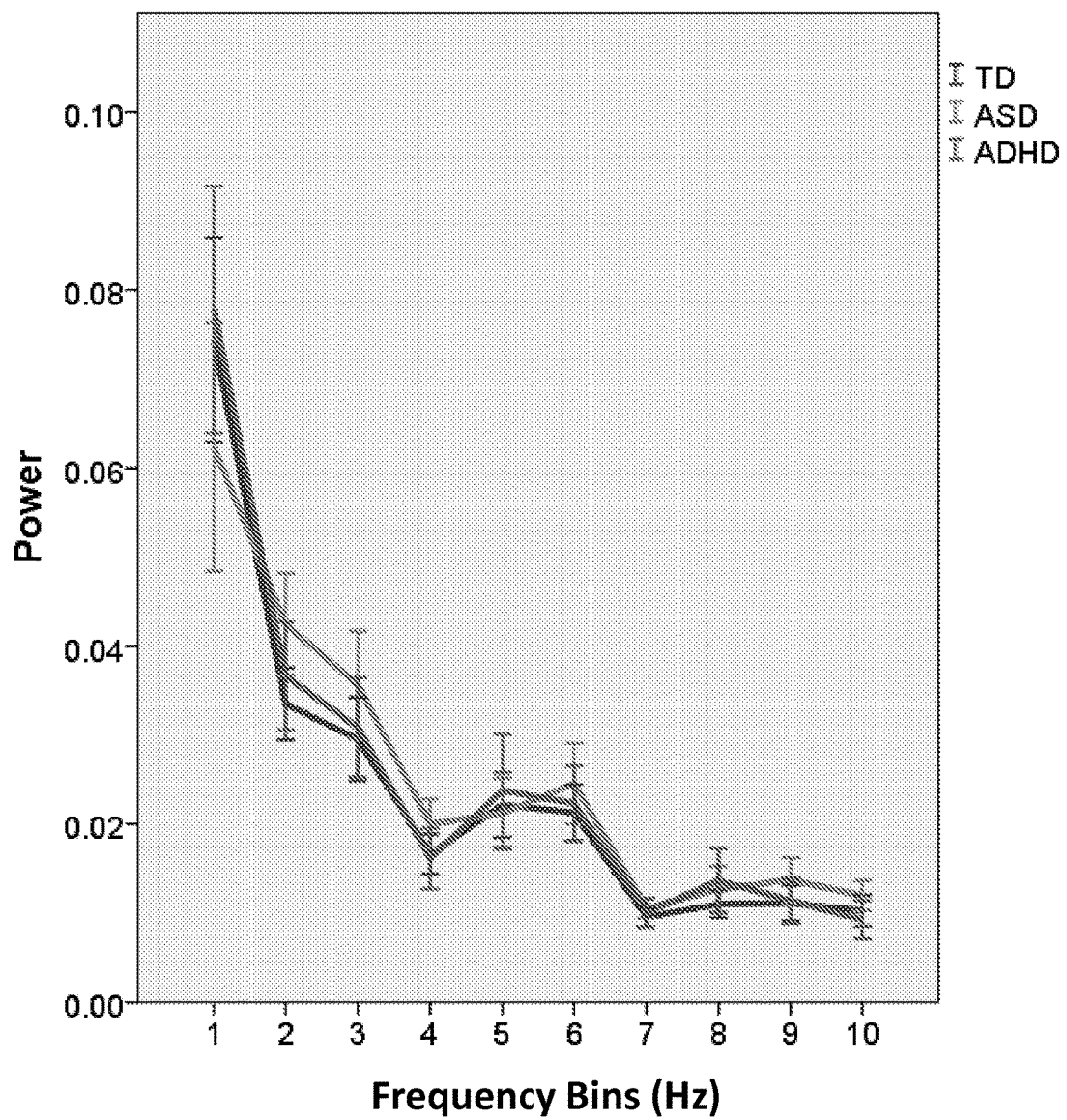

FIG. 1 illustrates a flow diagram showing an exemplary process for handwriting assessment, according to an embodiment of the present invention. As illustrated in FIG. 1 the method 10 includes a step 12 of selection of preset templates or a user defined template. Exemplary templates 14, 16 are illustrated in FIG. 1. Step 18 includes collection of digitized handwriting using a computing device equipped to receive written input from a stylus. Exemplary digitized handwriting 20, 22 is illustrated in FIG. 1. Optional step 24 includes real-time kinematic feedback, as illustrated in 26. The real time kinematic feedback can let the user know whether the user's pacing is too fast. Step 28 includes processing of the handwriting data. Processing can be done on the computing device receiving the input, on a server, a networked computer or server, a remote server, or the cloud. The data analysis 30 includes automated measurement of manual metrics 32, improved handwriting metrics 34, and new handwriting metrics 36. Manual metrics 32 include distance from guidelines (1), alignment (2), spacing (3), and size (4). These elements 1, 2, 3, and 4 are illustrated in 38. Improved handwriting metrics 34 include letter form. LDDMM provides a precise measure of the degree of deformation from the handwritten letter to the desired form. Improved handwriting metric analysis is illustrated in 40 and 42. New handwriting metrics 36 include letter kinematics (speed, ballisticity, tremor/fluency), time off the paper, and number of strokes per letter. These metrics are illustrated in 44 and 46 and FIGS. 2 and 3, which are enlarged views of 44 and 46 respectively. More particularly, FIGS. 2 and 3 illustrate graphical views of new handwriting metrics, according to an embodiment of the present invention.

Figure 4:
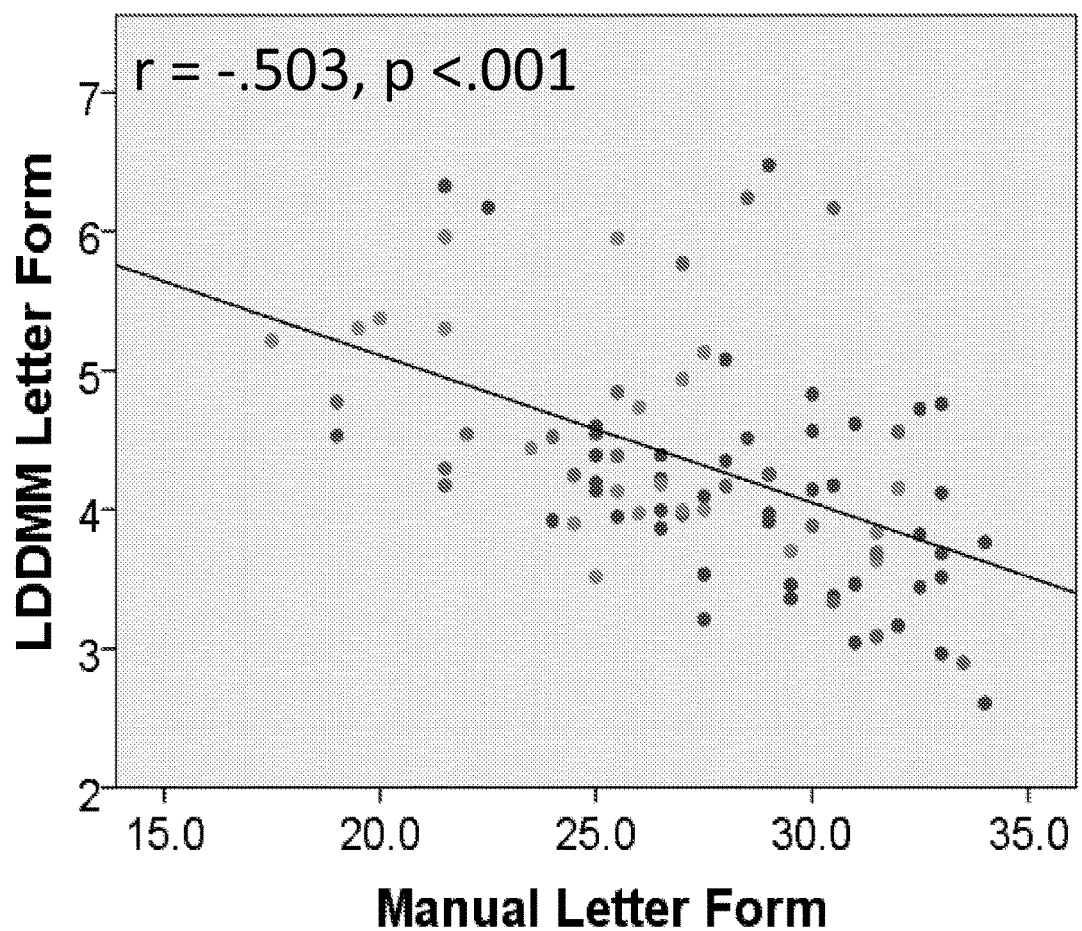
FIGS. 4 and 5 illustrate graphical views of automated versus manual results, according to an embodiment of the present invention.
Figure 5:
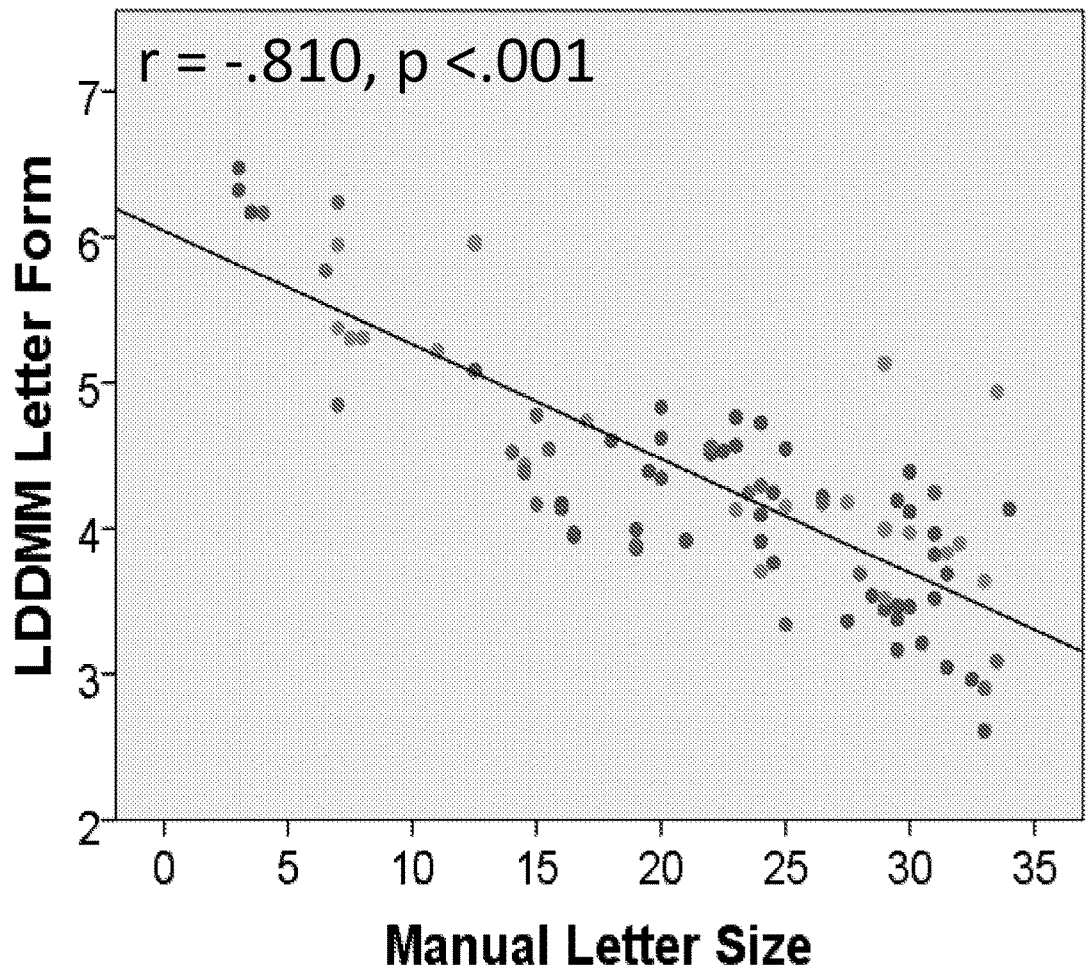

FIGS. 4 and 5 illustrate graphical views of automated versus manual results, according to an embodiment of the present invention. FIGS. 4 and 5 show Pearson Correlations between manually assessed letter form and size (x-axis; MHA) and LDDMM letter form (y-axis). Higher scores represent in all measures indicate worse performance. For the graphs.

It should be noted that data supports the method of the present invention. Writing performance was assessed using a digitizing tablet (Wacom Intuos4) in fifty-six children, 20 with ASD (17M and 3F) and 36 TD (29M and 7F), ages 8-12 years. Groups were balanced for age, gender, perceptual reasoning index, and socioeconomic status. Each participant completed a novel handwriting task based off the Minnesota Handwriting Assessment. In addition, each participant had to copy and trace 6 novel characters which were based off multiple non-latin alphabets. Using Matlab, handwriting data were segmented into letters to extract metrics of: Letter Speed, Speed Inflections, Letter Spacing, Letter Form, as well as spectral power at 4, 5, and 6 hz. Letter Form was analyzed using large deformation diffeomorphic metric mapping (LDDMM). Spectral power was assessed by doing a Fourier transform on the velocity curve for each letter. The average spectral power per 1 hz bin (i.e. 4, 5, & 6 hz) was calculated. Group differences were assessed using a repeated measures ANOVA (2 Group×2 Condition) for letter form, speed, speed inflection variability, letter spacing. A univariate ANOVA was used to assess group differences in the copy and trace conditions for spectral power measures. The relationship between handwriting kinematics and both Movement Assessment Battery for Children (mABC-2) and working memory index (WISC-IV) scores was investigated using Pearson's correlation.

The repeated measures ANOVA showed significant group differences for letter form ($F=0.7.877$, $p=0.007$), speed ($F=4.651$, $p=0.036$), and speed variability ($F=13.169$, $p=0.001$) but not letter spacing ($F=0.482$, $p=0.49$). Letter form, speed, and speed variability showed a significant effect of condition ($F>29.282$, $p<0.001$). Letter speed showed a significant condition×group interaction ($F=4.651$, $p=0.036$); both letter form and speed variability did not show a significant condition×group interaction. Post-hoc tests revealed significant differences in both copy and trace conditions for letter form (copy—$F=3.891$, $p=0.054$; trace—$F=13.779$, $p<0.001$) and speed variability (copy—$F=6.071$, $p=0.017$; trace—$F=10.639$, $p=0.002$). Letter speed only showed group differences in the Copy condition (copy—$F=6.706$, $p=0.012$; trace $F=0.351$, $p=0.556$). Analysis of the spectral power revealed significant increases in frequency bins 4 and 5 hz in the copy condition (4 hz bin—$12.534$, $p=0.001$; 5 hz bin—$F=8.842$, $p=0.005$; 6 hz bin—$F=2.762$, $p=0.104$) but not the trace condition. Pearson's correlations revealed significant correlations between letter form and working memory in the ASD group during the copy condition ($r=-0.720$, $p<0.001$) and trace condition ($r=-0.451$, $p=0.046$). The spectral power for the 4 hz bin in the copy condition was significantly correlated with mABC-2 Aiming and Catching Standard score ($r=-0.578 p=0.008$) and marginally correlated with the mABC-2's catching subscore ($r=-0.387$ $p=0.092$), but not the manual dexterity component score ($r=-0.215$, $p=0.362$). The typically developing group did not show and significant correlations.

These results suggest that children have difficulty with handwriting, specifically in letter formation and fluency in handwriting movements. Worse letter form was associated with decreased working memory (WISC-IV, WMI) and increased spectral power at 4-5 Hz was associated with worse motor control. An increase in 4-5 Hz periodicity has previously been associated with cerebellar impairments. These may suggest that reduced automaticity in handwriting in children with autism may be associated with motor control.

Figure 6:
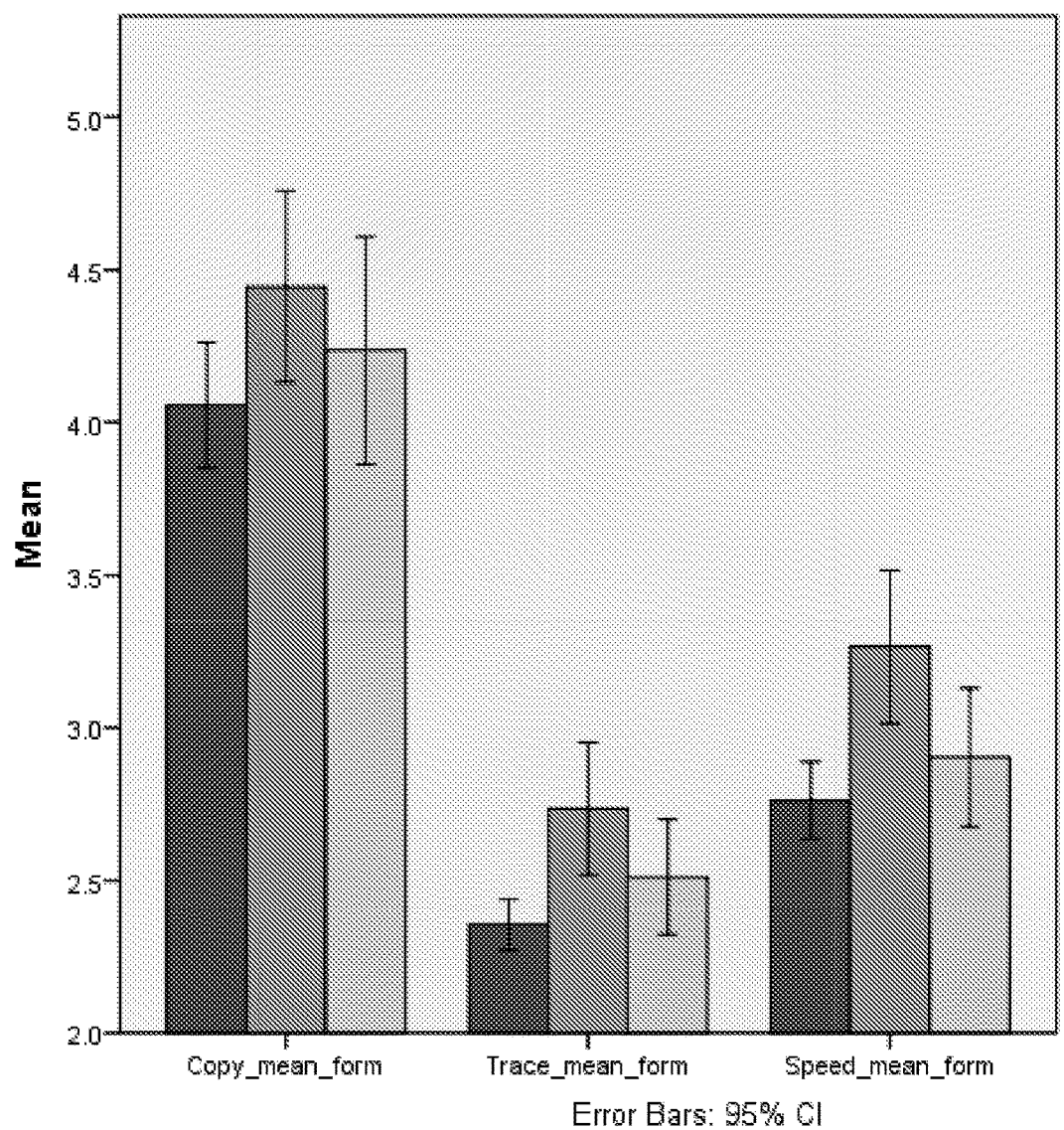
FIGS. 6 and 7 illustrate graphical views of letter form scores for English and Non-English assessments from students with TD, ASD, and ADHD.
Figure 7:
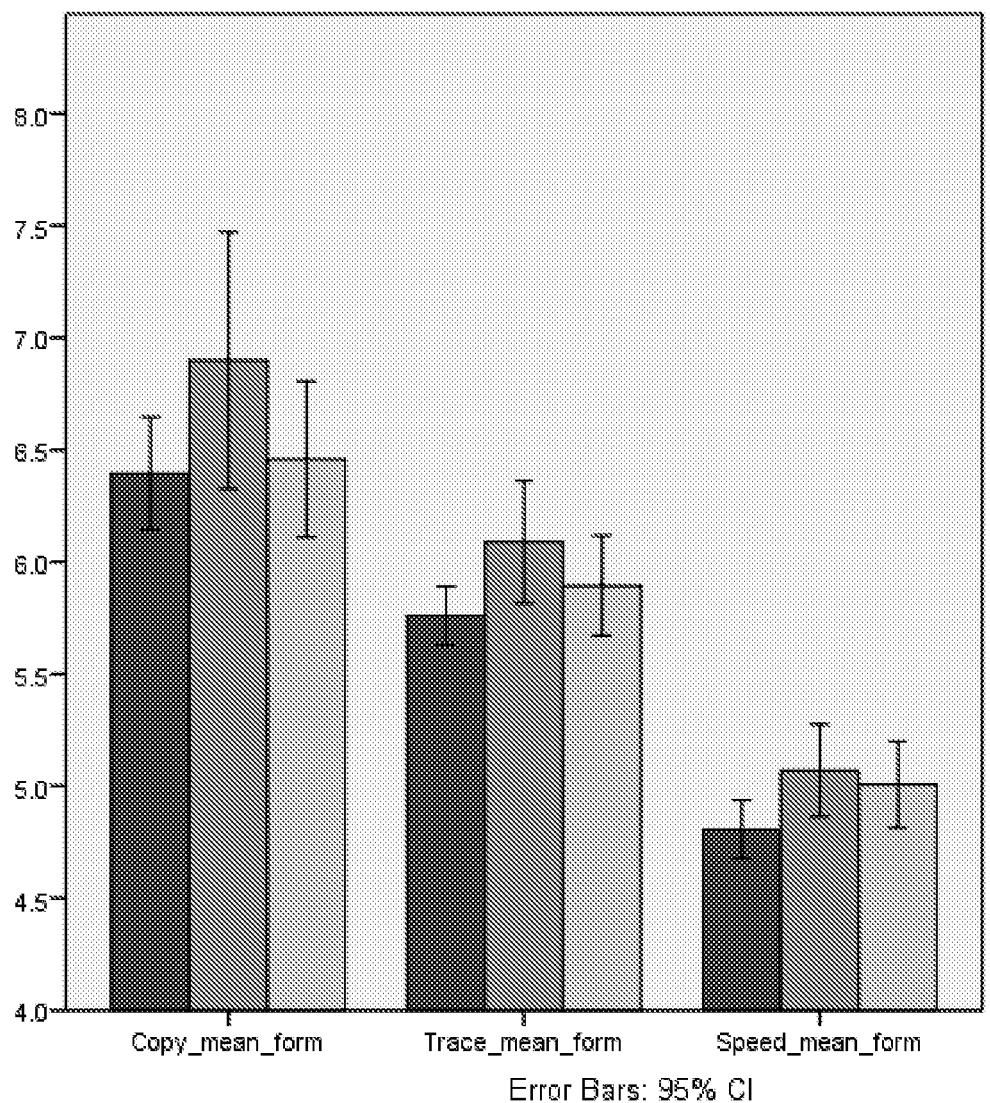

Consistent with the data above, the present invention in use revealed impairments in children with ASD compared with TD children across all tasks and conditions (English copy $p=0.031$, trace $p<0.001$, fast trace $p<0.001$; Non-English copy $p=0.062$, trace $p=0.014$, fast trace $p=0.021$; FIGS. 6 and 7), as well as significant differences between ASD and ADHD in the English fast trace condition ($p=0.036$; FIGS. 6 and 7). No group differences (TD, ASD, and ADHD) were observed in terms of handwriting kinematics. Letter form, in both tasks, was correlated with the WISC-IV's working memory index across all conditions in the ASD group ($p<0.008$) and with PANESS total score for the trace condition ($p<0.05$). These results may suggest decreased automaticity and greater recruitment of higher order cognitive systems (e.g. mPFC and DLPFC) in the ASD group. FIGS. 6 and 7 illustrate graphical views of letter form scores for English and Non-English assessments from students with TD, ASD, and ADHD. Standard error bars represent 2 S.E. above and below the mean. Stars signify $p<0.05$, double stars signify $p<0.01$, and plus signs represent $p<0.1$. Higher letter form scores signify worse performance. All children showed decreased performance in the copy condition compared to the trace conditions, while children with ASD show significant letter form impairments, relative to TD children, across conditions. All kinematic measures did not show an effect of diagnosis.

Figure 8:
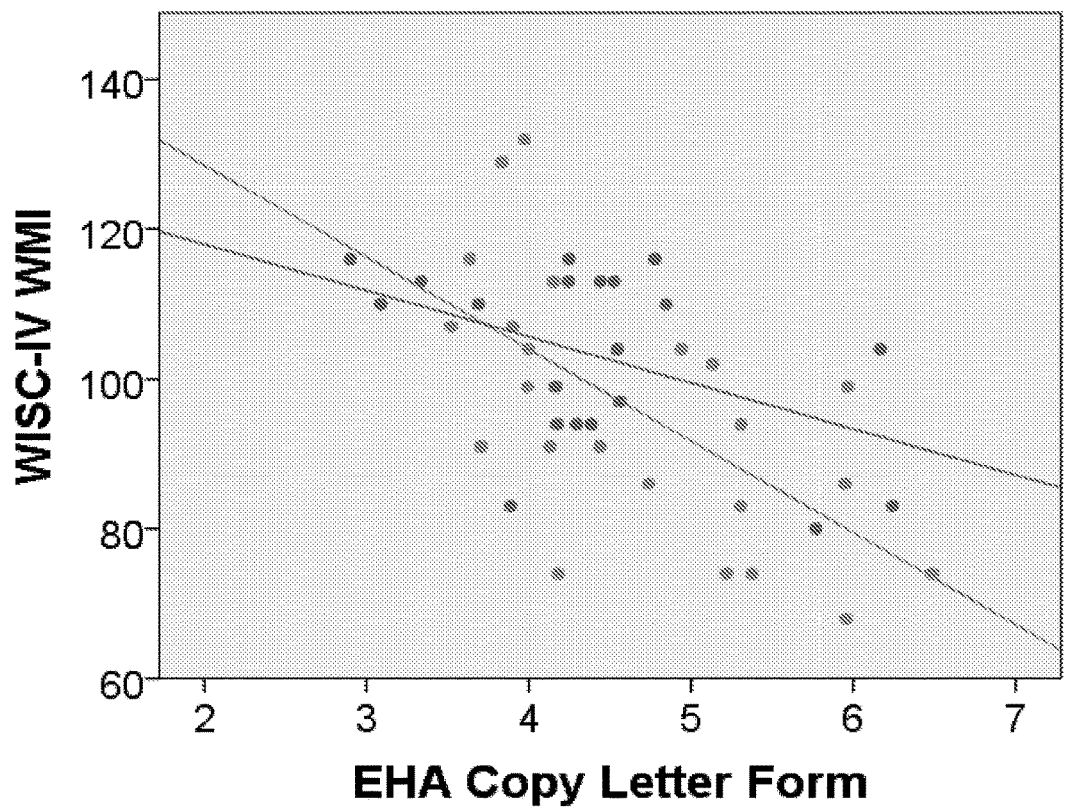
FIGS. 8 and 9 illustrate graphical views of the correlations between letter form scores in the English and Non-English copy conditions and working memory, as measured by the WISC-IV.
Figure 9:
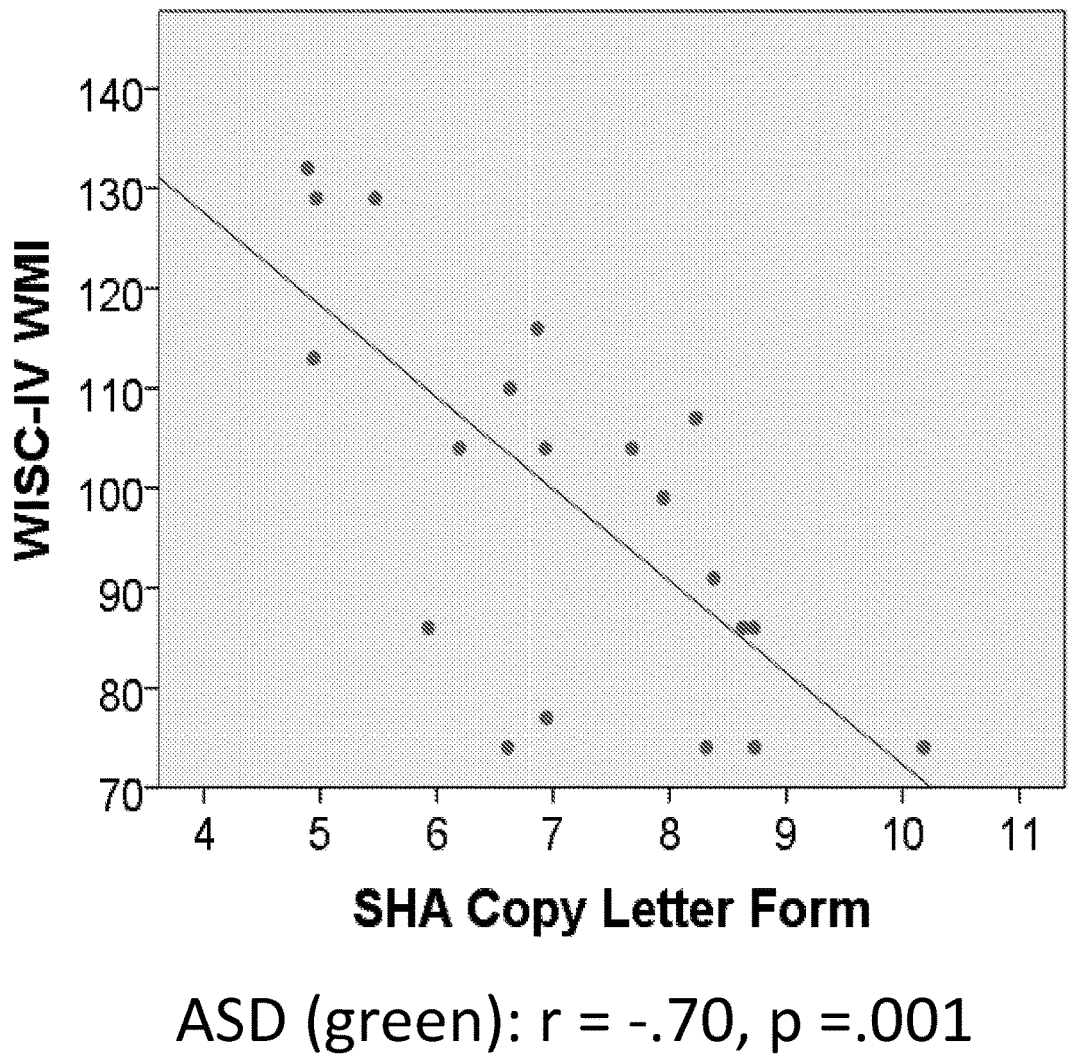

FIGS. 8 and 9 illustrate graphical views of English and symbol letter form correlations with WISC-IV working memory index, according to an embodiment of the present invention. FIGS. 8 and 9 illustrate Pearson Correlations between letter form (English, FIG. 8; Symbol, FIG. 9) and WISC-IV Working Memory Index (WMI). Higher letter form scores represent worse performance, while higher WMI scores represent better working memory.

It should be noted that the computer application is programmed onto a non-transitory computer readable medium that can be read and executed by any of the computing devices mentioned in this application. The non-transitory computer readable medium can take any suitable form known to one of skill in the art. The non-transitory computer readable medium is understood to be any article of manufacture readable by a computer. Such non-transitory computer readable media includes, but is not limited to, magnetic media, such as floppy disk, flexible disk, hard disk, reel-to-reel tape, cartridge tape, cassette tapes or cards, optical media such as CD-ROM, DVD, Blu-ray, writable compact discs, magneto-optical media in disc, tape, or card form, and paper media such as punch cards or paper tape. Alternately, the program for executing the method and algorithms of the present invention can reside on a remote server or other networked device. Any databases associated with the present invention can be housed on a central computing device, server(s), in cloud storage, or any other suitable means known to or conceivable by one of skill in the art. All of the information associated with the application is transmitted either wired or wirelessly over a network, via the internet, cellular telephone network, or any other suitable data transmission means known to or conceivable by one of skill in the art. The non-transitory computer readable medium can be executed on any computing device, such as a personal computer, a tablet, a smart phone, a computing device designed specifically for the present invention, or any other suitable device known to or conceivable by one of skill in the art.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A non-transitory computer readable medium storing instructions comprising:
    one or more instructions that, when executed by one or more processors, cause the one or more processors to:
        provide, via an interface of a device, a worksheet to a subject,
        the worksheet including one or more template writing characters;
        provide instructions to the subject to reproduce the one or more template writing characters provided in the worksheet to produce one or more reproduced writing characters;
        collect data related to the one or more reproduced writing characters,
            the data including morphometric data related to the one or more reproduced writing characters:
                the morphometric data related to the one or more writing characters including:
                    an overall form associated with the one or more reproduced writing characters,
                    a size associated with the one or more reproduced writing characters, and
                    a pitch associated with the one or more reproduced writing characters;
        analyze the morphometric data related to the one or more reproduced writing characters,
            the morphometric data related to the one or more reproduced writing characters being compared to data associated with a corresponding predefined template character,
            the overall form associated with the one or more reproduced writing characters being analyzed based upon large deformation diffeomorphic metric mapping (LDDMM) to determine a degree of letter deformation to match the one or more reproduced writing characters to the corresponding predefined template character; and
        transmit an assessment of the one or more reproduced writing characters based upon analyzing the morphometric data,
            the assessment including results of the analysis compared to population normalized measures.

2. The non-transitory computer readable medium of claim 1, where the one or more instructions, when executed by the one or more processors, further cause the one or more processors to:
    set a user defined speed threshold at which the subject is to reproduce the one or more reproduced writing characters; and
    notify the subject when a speed at which the subject reproduces the one or more reproduced writing characters exceeds the user defined speed threshold.

3. The non-transitory computer readable medium of claim 1, where the data related to the one or more reproduced writing characters includes kinematics data, and
    where the one or more instructions, when executed by the one or more processors, further cause the one or more processors to:
    analyze the kinematics data related to the one or more reproduced writing characters.

4. The non-transitory computer readable medium of claim 3, where the kinematics data related to the one or more reproduced writing characters includes:
    speed of producing the one or more reproduced writing characters,
    one or more velocity inflections,
    an acceleration to deceleration ratio,
    ballisticity, and
    a spectral power.

5. The non-transitory computer readable medium of claim 1, where the one or more instructions, when executed by the one or more processors, further cause the one or more processors to:

upload the data related to the one or more reproduced writing characters to a cloud-type server.

6. The non-transitory computer readable medium of claim 1, where the one or more instructions, when executed by the one or more processors, further cause the one or more processors to:
analyze kinematics data and the morphometric data in parallel.

7. The non-transitory computer readable medium of claim 1, where the one or more instructions, when executed by the one or more processors, further cause the one or more processors to:
provide instructions to the subject to use a stylus.

8. The non-transitory computer readable medium of claim 1, where the one or more instructions, when executed by the one or more processors, further cause the one or more processors to:
provide instructions to a user associated with the device to enter data related to the subject.

9. The non-transitory computer readable medium of claim 1, where the one or more instructions, when executed by the one or more processors, further cause the one or more processors to:
analyze the morphometric data to determine letter to letter spacing and letter to guideline spacing, the letter to letter spacing and letter to guideline spacing being compared to a predefined spacing template.

10. A computing device, comprising:
a user interface;
one or more memories; and
one or more processors, communicatively coupled to the one or more memories to:
provide, via the user interface, a worksheet to a subject, the worksheet including one or more template writing characters;
provide instructions to the subject to reproduce the one or more template writing characters presented in the worksheet;
receive data related to the one or more reproduced writing characters, the data being associated with morphometric data, the morphometric data including:
an overall form associated with the one or more reproduced writing characters,
a size associated with the one or more reproduced writing characters, and
a pitch associated with the one or more reproduced writing characters;
analyze the morphometric data related to the one or more reproduced writing characters, the morphometric data related to the one or more reproduced writing characters being compared to data associated with a corresponding predefined template character, the overall form associated with the one or more reproduced writing characters being analyzed based upon large deformation diffeomorphic metric mapping (LDDMM) to determine a degree of letter deformation required to match the one or more reproduced writing characters to the corresponding predefined template character; and
produce an assessment of the one or more reproduced writing characters, the assessment including results of the analysis compared to population normalized measures.

11. The computing device of claim 10, where the one or more processors are further to:
set a user defined speed threshold at which the subject is to reproduce the one or more reproduced writing characters; and
notify the subject when a speed at which the subject reproduces the one or more reproduced writing characters exceeds the user defined speed threshold.

12. The computing device of claim 10, where the data related to the one or more reproduced writing characters includes kinematics data, and
where the one or more processors are further to:
analyze the kinematics data related to the one or more reproduced writing characters.

13. The computing device of claim 12, where the kinematics data includes:
speed of producing the one or more reproduced writing characters,
one or more velocity inflections,
an acceleration to deceleration ratio,
ballisticity, and
spectral power.

14. The computing device of claim 10, where the one or more processors are further to:
upload the data related to the one or more reproduced writing characters to a cloud-type server.

15. The computing device of claim 10, where the one or more processors are further to:
analyze kinematics data and the morphometric data in parallel.

16. The computing device of claim 10, where the one or more processors are further to:
analyze the morphometric data to determine letter to letter spacing and letter to guideline spacing, the letter to letter spacing and letter to guideline spacing being compared to a predefined spacing template.

17. A method, comprising:
providing, via an interface of a device, a worksheet to a subject, the worksheet including a number of template writing characters;
providing, by the device, instructions to the subject to reproduce the template writing characters provided in the worksheet to produce one or more reproduced writing characters;
collecting, by the device, data related to the one or more reproduced writing characters, the data including morphometric data related to the one or more reproduced writing characters:
the morphometric data related to the one or more writing characters including:
an overall form associated with the one or more reproduced writing characters,
a size associated with the one or more reproduced writing characters, and
a pitch associated with the one or more reproduced writing characters;
analyzing, by the device, the morphometric data related to the one or more reproduced writing characters, the morphometric data related to the one or more reproduced writing characters being compared to data associated with a corresponding predefined template character, the overall form associated with the one or more reproduced writing characters being analyzed based upon large deformation diffeomorphic metric mapping (LDDMM) to determine a degree of letter deformation required to match the one or more reproduced writing characters to the corresponding predefined template character; and transmitting, by the device, an assessment of the reproduced writing characters based upon analyzing the morphometric data, the assessment including results of the analysis compared to population normalized measures to track handwriting performance.

18. The method of claim 17, where the data related to the one or more reproduced writing characters includes kinematics data, and further comprising:
analyzing the kinematics data to determine:
speed of producing the reproduced writing characters,
one or more velocity inflections,
an acceleration to deceleration ratio,
ballisticity, and
a spectral power.

19. The method of claim 18, where the kinematics data and morphometric data are analyzed in parallel.

20. The method of claim 18, where the kinematics data further includes:
a number of strokes per character; and
time off the worksheet.

21. The method of claim 17, further comprising:
setting a user defined speed threshold at which the subject is to reproduce the one or more reproduced writing characters; and
notifying the subject when a speed at which the subject reproduces the one or more reproduced writing characters exceeds the user defined speed threshold.

22. The method of claim 17, further comprising:
analyzing the morphometric data to determine letter to letter spacing and letter to guideline spacing, the letter to letter spacing and letter to guideline spacing being compared to a predefined spacing template.

* * * * *